United States Patent

Sauer et al.

[11] 4,017,545
[45] Apr. 12, 1977

[54] PROCESS FOR THE PREPARATION OF BICYCLOALKANE DERIVATIVES

[75] Inventors: Gerhard Sauer; Hans Peter Lorenz; Ulrich Eder; Gregor Haffer; Jurgen Ruppert; Rudolf Wiechert, all of Berlin, Germany

[73] Assignee: Schering Aktiengesellschaft, Berlin & Bergkamen, Germany

[22] Filed: June 20, 1974

[21] Appl. No.: 481,241

[30] Foreign Application Priority Data

June 21, 1973  Germany .......................... 2331997

[52] U.S. Cl. ..................... 260/590 FA; 260/476 C; 260/586 F; 260/340.5; 260/340.7; 260/340.9; 260/488 B; 260/307 H
[51] Int. Cl.² ........................................ C07C 49/76
[58] Field of Search .......... 260/590, 586 F, 586 E, 260/590 FA, 488 B, 476 C

[56] References Cited

UNITED STATES PATENTS

| | | | |
|---|---|---|---|
| 3,412,107 | 11/1968 | Radoje et al. ................... | 260/586 F |
| 3,692,803 | 9/1972 | Hojos ............................. | 260/340.5 |
| 3,703,479 | 11/1972 | Theimer ......................... | 260/586 F |
| 3,773,836 | 11/1973 | Hall ................................ | 260/586 F |
| 3,870,659 | 3/1975 | Bozyato et al. ................. | 260/586 F |

OTHER PUBLICATIONS

Gould, "Mechanism & Structure in Organic Chem.," pp. 258–264, 485–489 (1959).

Primary Examiner—James O. Thomas, Jr.
Assistant Examiner—James H. Reamer
Attorney, Agent, or Firm—Millen & White

[57] ABSTRACT

Bicycloalkanes useful as intermediates in the total synthesis of steroids of the formula

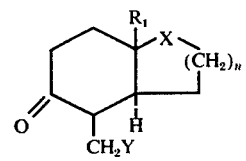

wherein $n$ is the integer 1 or 2; $R_1$ is lower-alkyl; X is free or ketalized carbonyl or free, esterified or etherified hydroxymethylene; and Y is $-SO_2-R_2$ or $-C(Z)(R_3)-R_4$ wherein $R_2$ is alkyl, aryl or aralkyl $R_3$ is H or lower-alkyl, $R_4$ is alkoxycarbonyl or acyl and Z is lower-alkoxycarbonyl, lower acyl, lower alkylsulfinyl or lower-alkylsulfonyl, are produced by the steps of hydrogenating a compound of the formula

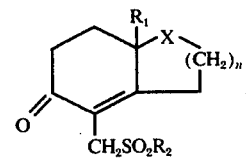

and condensing the thus-produced ring saturated compound with a salt of the formula $C(Z)(R_3)R_4^-Me^+$ wherein $n$, X, $R_1$, $R_2$, $R_3$, $R_4$ and Z have the values given above.

13 Claims, No Drawings

PROCESS FOR THE PREPARATION OF BICYCLOALKANE DERIVATIVES

BACKGROUND OF THE INVENTION

This invention relates to a process for the production of bicycloalkanes and to novel bicycloalkanes thus produced.

SUMMARY OF THE INVENTION

According to this invention, bicycloalkanes of the general Formula I

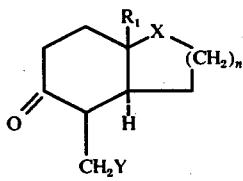

wherein $n$ is the integer 1 or 2; $R_1$ is lower alkyl; X is free or ketalized carbonyl or free, esterified, or etherified hydroxymethylene; and Y is $-SO_2-R_2$ or

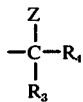

wherein $R_2$ is an alkyl, aryl, or aralkyl, $R_3$ is a hydrogen atom or lower alkyl, $R_4$ is alkoxycarbonyl or acyl, and Z is a lower alkoxycarbonyl, lower acyl, lower alkylsulfinyl, or lower alkylsulfonyl, are prepared by hydrogenating a compound of general Formula II

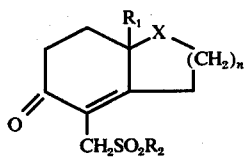

wherein $n$, X, $R_1$, and $R_2$ have the values given above, with hydrogen in the presence of a palladium-carbon catalyst and a lower alcohol or ketone, to produce a compound of general Formula I$a$

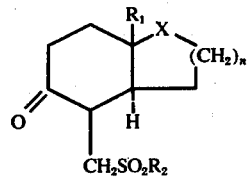

wherein $n$, X, $R_1$, and $R_2$ have the values given above, which compounds, when condensed in a nonpolar solvent with a salt of the general Formula III

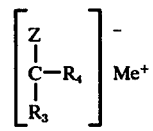

wherein Z, $R_3$, and $R_4$ have the values given above and Me$^+$ is an alkali or alkaline earth metal atom, are converted to compounds (I$b$) of Formula I wherein Y is $-C(Z)(R_3)-R_4$.

In its composition aspect, this invention relates to novel compounds of general Formula I$a$.

DETAILED DISCUSSION

The term "lower alkyl" as used herein means preferably alkyl of 1–4 carbon atoms, e.g., methyl, ethyl, propyl, isopropyl, butyl and tert.-butyl. Especially preferred $R_1$ and $R_3$ alkyl groups are methyl and ethyl.

The term "alkyl" as used herein preferably means alkyl of 1–12 carbon atoms. The term "aryl" preferably means mono- or dicyclic carbocyclic of up to 12 carbon atoms, e.g., phenyl or naphthyl. Equivalent of the unsubstituted phenyl and naphthyl are those substituted by methyl, methoxy, chlorine, bromine, and/or nitro. Examples of $R_2$ alkyl, aryl and aralkyl groups of up to 12 carbon atoms are methyl, ethyl, propyl, isopropyl, butyl, amyl, isoamyl, hexyl, heptyl, octyl, phenyl, o-, m-, and p-methylphenyl, p-methoxyphenyl, p-chlorophenyl, m-nitrophenyl, α- and/or β-naphthyl, benzyl, phenethyl and β-phenylpropyl.

The term "acyl" means preferably the acyl radical of a carboxylic acid, preferably hydrocarbon carboxylic acid, e.g., of 1–8 carbon atoms, which can be straight-chain or branched. Equivalent of the unsubstituted saturated hydrocarbon acyl are those which are unsaturated and/or substituted by free or esterified carboxyl groups, free, esterified, or etherified hydroxyl groups, chlorine or bromine atoms, free or ketalized oxo groups, or a 3,5-dialkylisoxazol-4-yl group.

Examples of $R_4$ groups are:

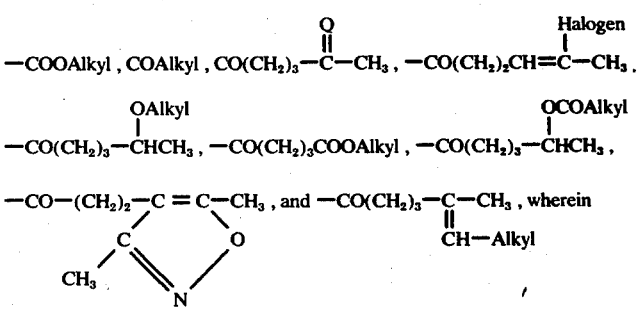

"Alkyl" is preferably alkyl of 1–4 carbon atoms, Q is an ethylenedioxy, propylenedioxy, dimethylpropylenedioxy, or phenylenedioxy group, and "Halogen" is a chlorine or bromine atom.

X can be a free or ketalized carbonyl or free, esterified, or etherified hydroxymethylene preferably in position β. Examples of ketalized carbonyl are 1,2- and 1,3-alkylenedioxymethylene of 1–8 carbon atoms in the alkylene group, e.g., 1,2-ethylenedioxymethylene, 1,3-propylenedioxymethylene, 2,3-butylenedioxymethylene, 2′,2′-dimethyl-1′,3′-propylenedioxymethylene, 2,4-pentylenedioxymethylene and 1,2-phenylenedioxymethylene. Examples of esterified hydroxymethylene are those wherein the ester preferably is an ester of a hydrocarbon carboxylic acid or hydrocarbonoxycarboxylic acid of 1–10 carbon atoms, for example, alkanoyloxy, including acetoxy, propionyloxy, butyryloxy, trimethylacetoxy, pentanoyloxy, hexanoyloxy, heptanoyloxy, octanoyloxy, benzoyloxy and benzyloxycarbonyloxy. Examples of preferred etherified hydroxymethylene X groups are alkoxymethylene and aralkoxymethylene of 1–10 carbon atoms in the alkoxy or aralkoxy group, e.g., methoxy, ethoxy, propoxy, butoxy, tert.-butoxy, isopropoxy, and benzyloxy.

Examples of preferred lower-alkoxycarbonyl, lower-alkylsulfinyl and lower-alkylsulfonyl and lower-acyl Z groups are those groups wherein the alkyl group is of 1–4 carbon atoms. Especially preferred are those wherein the alkyl group is methyl.

The first step of the process of this invention is conducted by hydrogenating a compound of general Formula II in the presence of a palladium-carbon catalyst and a lower alcohol or ketone to produce a compound of general Formula I$a$.

The lower alcohols or ketones are preferably those of up to 6 carbon atoms. Examples are methanol, ethanol, propanol, isopropanol, butanol, sec.-butanol, tert.-butanol, amyl alcohol or isoamyl alcohol, acetone, methyl ethyl ketone, diethyl ketone and methyl isobutyl ketone. The alcohol or ketone is employed as the hydrogenation solvent.

The hydrogenation is conducted using a conventional palladium-carbon catalyst.

In order to obtain a good yield in hydrogenated product, it is advantageous to admix a minor amount of a mineral acid, e.g., hydrochloric acid, sulfuric acid, phosphoric acid, or perchloric acid, to the reaction mixture. Preferably, 0.01% to 5.0% of mineral acid is added to the reaction mixture.

The hydrogenation is preferably conducted at a reaction temperature of 0°–80° C. and a hydrogen pressure of 1 atmosphere to 1000 atmospheres.

It is surprising that the hydrogenation of compounds of general Formula II, under the specific conditions of the process of this invention, occurs substantially completely and stereospecifically, and that the sulfone group is not affected.

It is basically possible to accomplish the hydrogenation of compounds of general Formula II under conditions other than those of the present invention. However, in such a case, the hydrogenation no longer takes place completely or substantially completely stereospecifically, and/or the sulfone group of the compounds is often split off.

Thus, the hydrogenation takes place incompletely, for example, when using as the catalyst palladium-calcium carbonate or palladium-barium sulfate, or when employing, for example, ethyl acetate, cyclohexane, dimethoxyethane, chloroform, or acetonitrile as solvent, instead of a lower alcohol or ketone. When using acetic acid as the solvent, considerable proportions of isomeric compounds are produced and if dimethylformamide or tetrahydrofuran is used as the solvent, the sulfonyl group is partially split off during the hydrogenation.

The condensation of a compound of general Formula I$a$ with a salt of general Formula III is conducted in a nonpolar solvent.

Suitable nonpolar solvents for this reaction step are, for example, aliphatic, cycloaliphatic and aromatic hydrocarbons of up to 12 carbon atoms, and dialkyl ethers of 4–12 carbon atoms. Examples of advantageous hydrocarbons and ethers are pentane, hexane, octane, petroleum ether, cyclopentane, cyclohexane, benzene, toluene, xylene, diethyl ether, diisopropyl ether and dibutyl ether.

The condensation of a compound of general Formula I$a$ with a salt of general Formula III can be conducted by first producing the salt by reacting the corresponding compound of general Formula IV

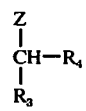

IV wherein Z, $R_3$, and $R_4$ have the values given above in one of the above-mentioned solvents, with an alkali or alkaline earth hydride, and subsequently treating the thus-formed salt with a compound of general Formula I$a$.

This reaction stage can also be effected by simultaneously reacting, in the above-mentioned solvents, a compound of general Formula I$a$, a compound of general Formula IV, and an alkali or alkaline earth hydride. This reaction step is preferably accomplished using 1–25 moles of base per mole of the compound of Formula IV.

Preferred alkali or alkaline earth hydrides are lithium hydride, sodium hydride, potassium hydride and calcium hydride.

The condensation is preferably conducted at a reaction temperature of 0° to 100° C.

Basically, it is likewise possible to effect the condensation in a polar solvent, e.g., dimethoxyethane, dimethylformamide, or ethanol. However, since under these conditions the compounds of general Formula I$a$ enter into self-condensations to a considerable extent, substantially lower yields of process products of general Formula I$b$ are obtained than with the use of the process of this invention.

The starting compounds of general Formula II required for the process of the present invention can be prepared, for example, by reacting a compound of general Formula V

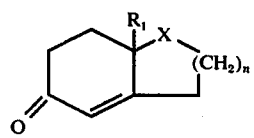

V wherein $n$, X, and $R_1$ have the values given above, either in triethanolamine with the corresponding hydroxymethylenesulfone, or by condensing the above compound in triethanolamine with paraformaldehyde and the corresponding mercaptan, and oxidizing the primarily formed thioether to the sulfone. See German Pat. application No. P 22 21 704, and U.S. Ser. No. 317,549 filed Dec. 22, 1972.

Compounds of general Formula Ib produced according to

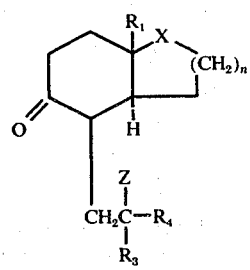

wherein n, X, Z, $R_1$, $R_3$, and $R_4$ have the values given above, which can be produced according to the process of this invention, are valuable intermediates suitable, in particular, for the total synthesis of steroids. See Belgian Pat. No. 739,718 and German Pat. application P 22 21 704, and U. S. Ser. No. 317,549 filed Dec. 22, 1972.

In the compound of Formula Ib wherein the substituent $R_4$ is an alkoxycarbonyl group or an optionally substituted acyl group, the substituent Z can be eliminated using various techniques apparent to those skilled in the art. For example, nitrile or alkoxycarbonyl Z groups can be saponified, and the thus-formed β-ketocarboxylic acids can be decarboxylated. Lower alkanoyl groups can be eliminated under the conditions customary for the keto splitting of β-diketones. Lower alkylsulfinyl and lower alkylsulfonyl Z groups can be eliminated by the Raney nickel desulfuration method. The thus-obtained compounds and their further conversion into steroids are conventional.

The compounds of general Formula Ib, wherein $R_4$ is an optionally substituted phenyl residue are 9,10-seco-1,3,5(10),8(14)-estratetraene derivatives. These compounds can be hydrogenated in a conventional manner to the corresponding 9,10-seco-1,3,5(10)-estratrienes which can then be cyclized in a manner known per se to the corresponding 1,3,5(10)-estratriene derivatives. Subsequently, the substituent Z present in the 6-position of the estratriene can be eliminated in a conventional manner.

Thus, for example, the 6-nitro steroids can be converted into the corresponding 6-keto steroids by means of the Nef reaction; the keto group of these steroids can be eliminated by hydrogenation, Clemmensen reduction, or equivalent methods.

The lower alkylsulfinyl groups or lower alkylsulfonyl groups present in the 6-position can be eliminated, for example, by Raney nickel desulfuration.

The 6-acyl steroids can be converted into the corresponding esters, for example, with the aid of the Bayer-Villiger rearrangement.

Nitrile or alkoxycarbonyl groups present in the 6-position can be converted, optionally after saponification, into 6-amino groups by means of Hofmann degradation or equivalent methods; the amino groups can then be eliminated by means of hydrogenation.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1 a. 0.56 g. of 1 β-tert.-butoxy-7aβ-methyl-5,6,7,7a-tetrahydroindan-5-one is combined with 0.44 g. of phenylhydroxymethylsulfone and 2 ml. of triethanolamine and heated in a nitrogen atmosphere under agitation to 100° C. for 16 hours.

The mixture is then allowed to cool, distributed between ether and water, the separated ether phase is dried and concentrated under vacuum. The residue is chromatographed on silica gel, recrystallized from ether, and the product is 0.24 g. of 1 β-tert.-butoxy-7aβ-methyl-4-(phenylsulfonylmethyl)-5,6,7,7a-tetrahydroindan-5-one, m.p. 133°–134° C.

$[\alpha]_D^{20} = +56°$ (chloroform; c = 1%).

b. 1.0 g. of 1 β-tert.-butoxy-7aβ-methyl-4-(phenylsulfonylmethyl)-5,6,7,7a-tetrahydroindan-5-one is combined with 50 ml. of ethanol, 5 ml. of 1N aqueous hydrochloric acid, and 100 mg. of palladium-animal charcoal (10%) and hydrogenated at 20° C. and under normal pressure.

After the reaction is terminated, the catalyst is filtered off, the solution is concentrated under vacuum, the residue is distributed between chloroform and aqueous sodium bicarbonate solution, the separated chloroform phase is concentrated under vacuum, and the residue is recrystallized from diisopropyl ether/hexane, thus obtaining 0.75 g. of 1 β-tert.-butoxy-7aβ-methyl-4-(phenylsulfonylmethyl)-perhydroindan-5-one, m.p. 104°–106° C.

$[\alpha]_D^{20} = +39°$ (chloroform; c = 1%).

c. 380 mg. of 1 β-tert.-butoxy-7aβ-methyl-4-(phenylsulfonylmethyl)-perhydroindan-5-one is combined with 0.4 ml. of 3-oxo-7,7-(ethylenedioxy)-octanoic acid ethyl ester, 100 mg. of sodium hydride (80% as an oil dispersion), and 70 ml. of absolute pentane, and refluxed for 30 minutes.

Thereafter, the reaction mixture is mixed with ice, acidified with acetic acid, extracted with chloroform, and the chloroform phase concentrated under vacuum, thus producing 490 mg. of 1 β-tert.-butoxy-7aβ-methyl-4-(2'-ethoxycarbonyl-3'-oxo-6',6'-ethylenedioxyheptyl)-perhydroindan-5-one as the crude product.

The thus-obtained crude product is combined, without further purification, with 4 ml. of 20% aqueous sodium hydroxide solution and 20 ml. of methanol and allowed to stand for 30 minutes at room temperature. The reaction mixture is then extensively concentrated, the residue acidified with acetic acid, saturated with NaCl, and the mixture extracted with ethyl acetate. The ethyl acetate phase is dried, concentrated, thus obtaining 8-carboxy-3β-tert.-butoxy-3aβ-methyl-6-(3',3'-ethylenedioxybutyl)-7-oxo-1,2,3,3a,4,5,7,8,9,10-decahydrobenz[e]indene as the crude product.

This crude product is dissolved in 25 ml. of benzene without any further purification and refluxed for one hour. Then the solution is concentrated, the residue is purified by chromatography over a silica gel column, the product being 320 mg. of 3β-tert.-butoxy-3aβ-methyl-6-(3′,3′-ethylenedioxybutyl)-7-oxo-1,2,3,3a,4,5,7,8,9,10-decahydrobenz[e]indene, m.p. 60°–66° C.

$[\alpha]_D^{20} = -14°$ (chloroform; c = 1%).

EXAMPLE 2 a. Under the conditions described in Example 1(a), 0.68 g. of 1β-benzoyloxy-7aβ-methyl-5,6,7,7a-tetrahydroindan-5-one is reacted with phenylhydroxymethylsulfone and worked up, yielding 0.53 g. of 1β-benzoyloxy-7aβ-methyl-4-(phenylsulfonylmethyl)-5,6,7,7a-tetrahydroindan-5-one, m.p. 159°–161° C.

b. Under the conditions set forth in Example 1(b), 1.0 g. of 1 β-benzoyloxy-7aβ-methyl-5,6,7,7a-tetrahydroindan-5-one is hydrogenated and worked up, thus obtaining 530 mg. of 1β-benzoyloxy-7aβ-methyl-4-(phenylsulfonylmethyl)-perhydroindan-5-one, m.p. 167°–168° C.

$[\alpha]_D^{20} = +67°$ (chloroform; c = 1%).

c. 380 mg. of 1β-benzoyloxy-7aβ-methyl-4-(phenylsulfonylmethyl)-perhydroindan-5-one is combined with 0.4 ml. of the ethyl ester of 3-oxo-7,7-(ethylenedioxy)-octanoic acid, 100 mg. of sodium hydride (80% oil dispersion), 60 ml. of pentane, and 25 ml. of benzene; the mixture is refluxed for 30 minutes and then worked up as described in Example 1(c), thus producing, as a crude product, 1β-benzoyloxy-7aβ-methyl-4-(1′-ethoxycarbonyl-2′-oxo-6′,6′-ethylenedioxyheptyl)-perhydroindan-5-one.

The thus-obtained crude product is combined with 4 ml. of 20% sodium hydroxide solution and 20 ml. of methanol and allowed to stand for 2 hours at room temperature. The reaction mixture is then worked up and the thus-produced crude product is decarboxylated as described in Example 1(c), yielding 365 mg. of 3β-hydroxy-3aβ-methyl-6-(3′,3′-ethylenedioxybutyl)-7-oxo-1,2,3,3a,4,5,7,8,9-10-decahydrobenz[e]indene as an oil.

$\epsilon_{249} = 13,700$. IR: bands at 2.9 μ and 6.0 μ.

EXAMPLE 3 a. 0.83 g. of 1β-hydroxy-7aβ-methyl-5,6,7,7a-tetrahydroindan-5-one, 0.15 g. of paraformaldehyde, and 0.6 ml. of phenylmercaptene are dissolved in 1.7 ml. of triethanolamine and heated for 8 hours to 110° C. The mixture is then combined with 5 ml. 1N sodium hydroxide solution, extracted with ether, the ether phase washed, dried, and concentrated under vacuum; yield: 1.25 g. of 1β-hydroxy-7aβ-methyl-4-(phenylthiomethyl)-5,6,7,7a-tetrahydroindan-5-one as a crude product.

500 ml. of this crude product is dissolved in 10 ml. of dimethoxyethane and combined with a solution of 1.1 ml. of 40% peracetic acid in 5 ml. of dimethoxyethane. Then, water, is added to the reaction mixture; the latter is extracted with chloroform, the chloroform phase is washed and concentrated under vacuum. The residue is recrystallized from ether, thus obtaining 420 mg. of 1β-hydroxy-7aβ-methyl-4-(phenylsulfonylmethyl)-5,6,7,7a-tetrahydroindan-5-one, m.p. 125°–126° C.

$[\alpha]_D^{20} = +72°$ (chloroform; c = 1%).

b. Under the same conditions as indicated in Example 1(b), 1.0 g. of 1β-hydroxy-7aβ-methyl-4-(phenylsulfonylmethyl)-5,6,7,7a-tetrahydroindan-5-one is hydrogenated, thus obtaining 700 mg. of 1β-hydroxy-7aβ-methyl-4-(phenylsulfonylmethyl)-perhydroindan-5-one as an oil. IR: bands at 2.8 μ, 5.8 μ, 7.56 μ, and 8.79 μ.

c. 1.05 g. of 1β-hydroxy-7aβ-methyl-4-(phenylsulfonylmethyl)-perhydroindan-5-one is combined with 1 ml. of the ethyl ester of 3-oxo-7,7-ethylenedioxy)-octanoic acid, 50 mg. of lithium hydride, 100 ml. of pentane, and 60 ml. of benzene; the mixture is refluxed for 30 minutes.

The reaction mixture is then worked up, cyclized, and the thus-obtained products are decarboxylated as described in Example 1(c), yielding 917 g. of 3β-hydroxy-3aβ-methyl-6-(3′,3′-ethylenedioxybutyl)-7-oxo-1,2,3,3a,4,5,7,8,9,10-decahydrobenz[e]indene, identical with the product obtained according to Example 2(c).

EXAMPLE 4 a. 1.18 g. of 1β-tert.-butoxy-7aβ-ethyl-5,6,7,7a-tetrahydroindan-5-one is reacted under the conditions described in Example 1(a), thus obtaining 0.56 g. of 1β-tert.-butoxy-7aβ-ethyl-4-(phenylsulfonylmethyl)-5,6,7,7a-tetrahydroindan-5-one, m.p. 128° C.

$[\alpha]_D^{20} = +42°$ (chloroform; c = 1%).

b. 1.0 g. of 1β-tert.-butoxy-7aβ-ethyl-4-(phenylsulfonylmethyl)-5,6,7,7a-tetrahydroindan-5-one is hydrogenated under the conditions set forth in Example 1(b), thus obtaining 650 mg. of 1β-tert.-butoxy-7aβ-ethyl-4-(phenylsulfonylmethyl)-perhydroindan-5-one, m.p. 135°–136° C.

$[\alpha]_D^{20} = +39°$ (chloroform; c = 1%).

c. 180 mg. of 1β-tert.-butoxy-7aβ-ethyl-4-(phenylsulfonylmethyl)-perhydroindan-5-one is reacted under the conditions described in Example 1(c), yielding 145 mg. of 3β-tert.-butoxy-3aβ-ethyl-6-(3′,3′-ethylenedioxybutyl)-7-oxo-1,2,3,3a,4,5,7,8,9,10-decahydrobenz[e]indene as an oil.

$\epsilon_{249} = 13,500$. IR: band at 6.0 μ.

EXAMPLE 5 a. 1.11 g. of 1β-tert.-butoxy-7aβ-methyl-5,6,7,7a-tetrahydroindan-5-one is combined with 1.0 ml. of 1-hexylmercaptan, 0.3 g. of paraformaldehyde, and 2 ml. of triethanolamine and heated for 20 hours to 110° C. The reaction mixture is worked up as described in Example 2(a), thus obtaining 1.1 g. of 1β-tert.-butoxy-7aβ-methyl-4-(1′-hexylthiomethyl)-5,6,7,7a-tetrahydroindan-5-one as an oil.

0.45 g. of 1β-tert.-butoxy-7aβ-methyl-4-(1′-hexylthiomethyl)-5,6,7,7a-tetrahydroindan-5-one is oxidized as set forth in Example 2(a), thus producing 0.42 g. of 1β-tert.-butoxy-7aβ-methyl-4-(1′-hexylsulfonylmethyl)-5,6,7,7a-tetrahydroindan-5-one, m.p. 51°–54.5° C.

$[\alpha]_D^{20} = +22°$ (chloroform; c = 1%).

b. Under the conditions indicated in Example 1(b), 1.0 g. of 1β-tert.-butoxy-7aβ-methyl-4-(1′-hexylsulfonylmethyl)-5,6,7,7a-tetrahydroindan-5-one is hydrogenated, thus obtaining 710 mg. of 1β-tert.-butoxy-7aβ-methyl-(1′-hexylsulfonylmethyl)-perhydroindan-5-one in the form of an oil.

IR: bands at 7.58 μ and 8.8 μ.

c. Under the conditions set forth in Example 1(c), 210 mg. of 1β-tert.-butoxy-7aβ-methyl-(1′-hexylsulfonylmethyl)-perhydroindan-5-one is reacted, thus producing 150 mg. of 3β-tert.-butoxy-3aβ-methyl-6-(3′,3′-ethylenedioxybutyl)-7-oxo-1,2,3,3a,4,5,7,8,9,10-decahydrobenz[e]indene, which is identical with the product obtained according to Example 1(c).

EXAMPLE 6

380 mg. of 1β-tert.-butoxy-7aβ-methyl-4-(phenysulfonylmethyl)-perhydroindan-5-one is combined with 0.4 ml. of the ethyl ester of 3-oxo-7-chloro-6-octenoic acid, 100 mg. of sodium hydride (80% oil dispersion), and 70 ml. of pentane and refluxed for 30 minutes. The reaction mixture is worked up, and the thus-obtained products are cyclized and decarboxylated as described in Example 1(c), thus obtaining 350 mg. of 3β-tert.-butoxy-3aβ-methyl-6-(3-chloro-2-butenyl)-7-oxo-1,2,3,3a,4,5,7,8,9,10-decahydrobenz[e]indene as an oil.

$\epsilon_{250} = 13,200$. IR: band at 6.0 μ.

EXAMPLE 7

380 mg. of 1β-tert.-butoxy-7aβ-methyl-4-(phenysulfonylmethyl)-perhydroindan-5-one is refluxed for 30 minutes with 0.4 g. of methyl-(2-oxo-6,6-phenylenedioxyheptyl)-sulfoxide, 200 mg. of sodium hydride (80% oil dispersion), and 80 ml. of benzene. The reaction mixture is then worked up and the thus-obtained product is cyclized as described in Example 1(c), yielding 300 mg. of 3β-tert.-butoxy-3aβ-methyl-6-(3',3'-phenylenedioxybutyl)-7-oxo-8-(methylsulfinyl)-1,2,3,3a,4,5,7,8,9,10-decahydrobenz[e]indene as an oil. $\epsilon_{248} = 13,100$. IR: bands at 5.86 μ, 6.0 μ, 6.78 μ, and 8.10 μ.

EXAMPLE 8

1.0 g. of 1β-tert.-butoxy-7aβ-methyl-4-(phenylsulfonylmethyl)-5,6,7,7a-tetrahydroindan-5-one is combined with 50 ml. of acetone and 0.5 ml. of perchloric acid and hydrogenated under the conditions disclosed in Example 1(b). The reaction mixture is then worked up, thus obtaining 730 mg. of 1β-tert.-butoxy-7aβ-methyl-4-(phenylsulfonylmethyl)-perhydroindan-5-one which is identical with the compound prepared according to Example 1(b).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A bicycloalkane of the formula

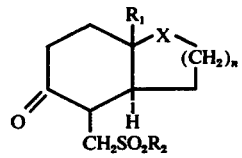

wherein n is the integer 1 or 2; $R_1$ is alkyl of 1–4 carbon atoms inclusive; $R_2$ is alkyl, mono- or dicyclic carbocyclic aryl or aralkyl, each of up to 12 carbon atoms, X is β-hydroxymethylene, 1-β-alkoxymethylene wherein alkoxy is of 1–4 carbon atoms or 1-β-hydrocarbonrcarbonyloxymethylene of 1–10 carbon atoms in the hydrocarbon group.

2. A compound of claim 1, wherein n is 1.
3. A compound of claim 1, wherein $R_1$ is $CH_3$ or $C_2H_5$.
4. A compound of claim 1, wherein $R_2$ is phenyl or alkyl of up to 12 carbon atoms.
5. A compound of claim 1, wherein X is β-hydroxymethylene.
6. A compound of claim 1, wherein X is 1-β-alkoxymethylene wherein alkoxy is of 1–4 carbon atoms.
7. A compound of claim 1, wherein X is 1-β-hydrocarboncarbonyloxymethylene of 1–10 carbon atoms.
8. A compound of claim 6, wherein n is 1, $R_1$ is $CH_3$ or $C_2H_5$ and $R_2$ is phenyl or alkyl of up to 12 carbon atoms.
9. A compound of claim 1, 1β-tert.butoxy-7aβ-methyl-4-(phenylsulfonylmethyl)-perhydroindan-5-one.
10. A compound of claim 6 wherein $R_2$ is phenyl.
11. A compound of claim 10 wherein $N$ is/and $R_1$ is $CH_3$ or $C_2H_5$.
12. A compound of claim 1, 1β-tert.-butoxy-7aβ-ethyl-4-(phenylsulfonylmethyl)-perhydroindan-5-one.
13. A compound of claim 1, 1β-tert.-butoxy-7aβ-methyl-(1'-hexylsulfonylmethyl)-perhydroindan-5-one.

* * * * *

UNITED STATES PATENT AND TRADEMARK OFFICE
CERTIFICATE OF CORRECTION

PATENT NO. : 4,017,545
DATED : April 12, 1977
INVENTOR(S) : GERHARD SAUER ET AL.

It is certified that error appears in the above-identified patent and that said Letters Patent are hereby corrected as shown below:

Claim 11, column 10, line 40: "N is/and $R_1$" should read

-- N is 1 and $R_1$ --.

Signed and Sealed this

Fourteenth Day of June 1977

[SEAL]

*Attest:*

RUTH C. MASON
*Attesting Officer*

C. MARSHALL DANN
*Commissioner of Patents and Trademarks*